US00PP18148P2

(12) United States Plant Patent
Pan

(10) Patent No.: US PP18,148 P2
(45) Date of Patent: Oct. 30, 2007

(54) ***LANTANA* PLANT NAMED 'BANTE ROSSA'**

(50) Latin Name: *Lantana camara*
Varietal Denomination: Bante Rossa

(75) Inventor: Shifeng Pan, Hollister, CA (US)

(73) Assignee: Goldsmith Seeds, Inc., Gilroy, CA (US)

( * ) Notice: Subject to any disclaimer, the term of this patent is extended or adjusted under 35 U.S.C. 154(b) by 0 days.

(21) Appl. No.: 11/406,006

(22) Filed: Apr. 18, 2006

(51) Int. Cl.
*A01H 5/00* (2006.01)

(52) U.S. Cl. ..... Plt./227

(58) Field of Classification Search ..... Plt./227
See application file for complete search history.

*Primary Examiner*—Kent Bell
*Assistant Examiner*—Annette H Para
(74) *Attorney, Agent, or Firm*—Jondle & Associates, P.C.

(57) ABSTRACT

A *lantana* plant particularly distinguished by large purple-pink and yellow flowers, a continuous, abundant and mid-season flowering response, medium green foliage with ovate leaves, vigorous growth, a medium to tall, spreading and mounding plant habit, and good branching ability, is disclosed.

3 Drawing Sheets

Genus and species: *Lantana camara.*
Variety denomination: 'Bante Rossa'.

BACKGROUND OF THE NEW PLANT

The present invention comprises a new and distinct cultivar of *lantana,* botanically known as *Lantana camara* and hereinafter referred to by the cultivar name 'Bante Rossa'. The new cultivar originated from a hybridization made in October 2002 in Gilroy, Calif. The female parent was '22-1', a proprietary rose-flowered *lantana* plant (unpatented), while the male parent was 'F13-1', a proprietary pink-flowered *lantana* plant (unpatented).

The new cultivar was created in October 2002 in Gilroy, Calif. and has been asexually reproduced repeatedly by vegetative cuttings and tissue culture in Gilroy, Calif. over a two and one-half-year period. The plant has also been trialed at Gilroy, Calif., Andijk, The Netherlands and Hillscheid, Germany. The present invention has been found to retain its distinctive characteristics through successive asexual propagations.

Plant Breeder's Rights for this cultivar have been applied for in Canada on Jul. 19, 2005 and with the European Union on Oct. 14, 2005.

SUMMARY OF THE INVENTION

The following are the most outstanding and distinguishing characteristics of the new cultivar when grown under normal horticultural practices in Gilroy, Calif. and Hillscheid, Germany.

1. Large purple-pink and yellow flowers;
2. A continuous, abundant and mid-season flowering response;
3. Medium green foliage with ovate leaves;
4. Vigorous growth;
5. A medium to tall, spreading and mounding plant habit; and
6. Good branching ability.

DESCRIPTION OF THE PHOTOGRAPHS

This new *lantana* plant is illustrated by the accompanying photographs which show overall plant habit including blooms, buds and foliage of the plant; the colors shown are as true as can be reasonably obtained by conventional photographic procedures. The photos are of 19- to 20-week-old plants in mid-July.

DESCRIPTION OF THE NEW CULTIVAR

Figure 1:
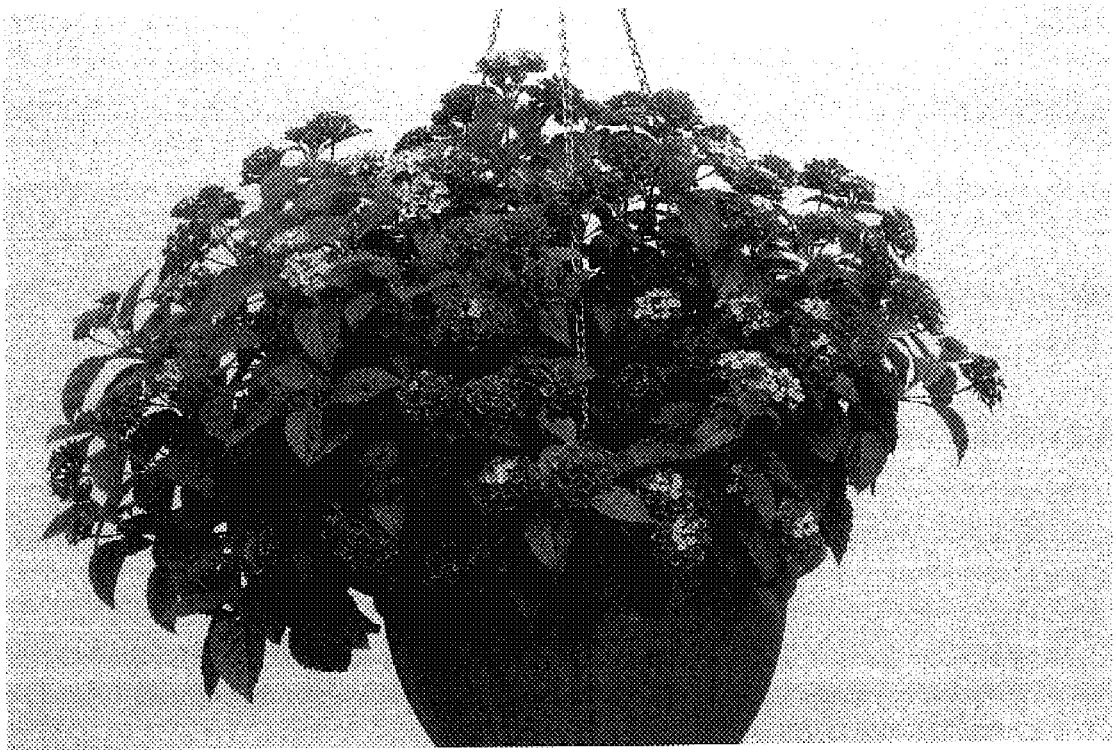
FIG. 1 shows the overall plant habit, including inflorescences, buds and foliage of three plants in a hanging basket.
Figure 2:
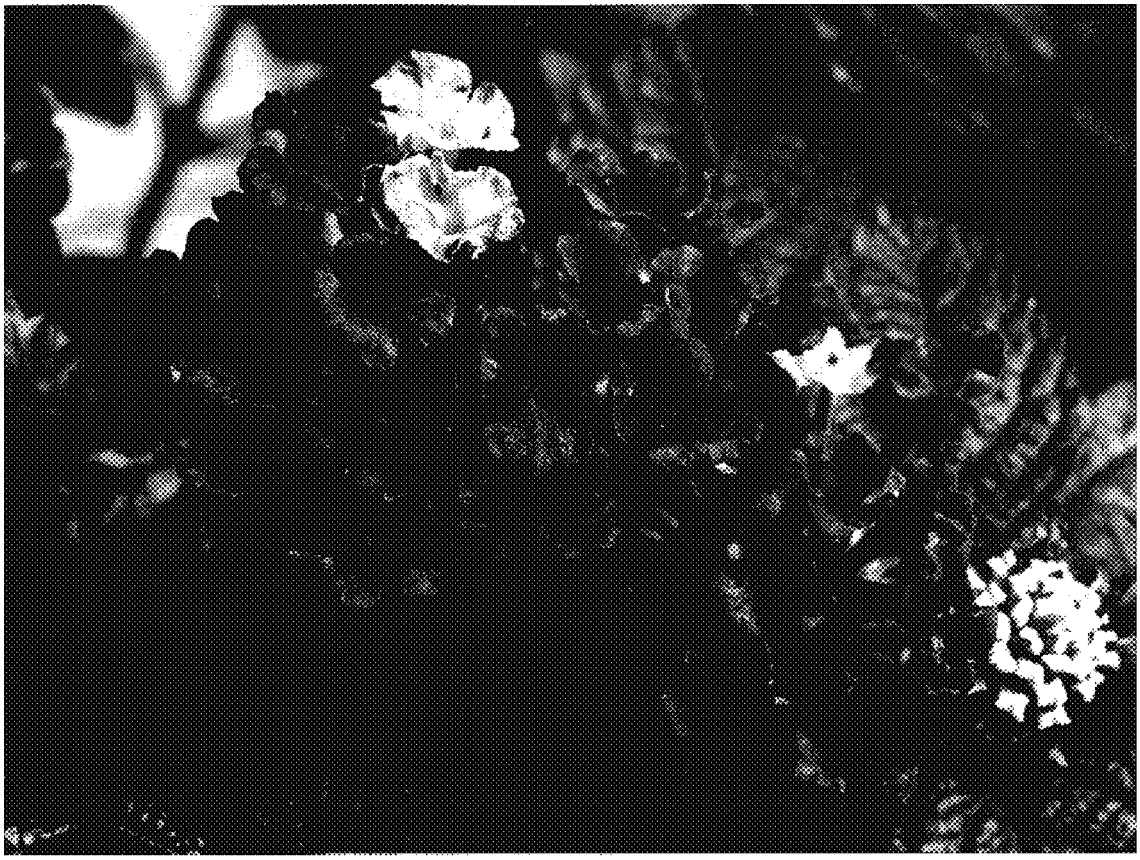
FIG. 2 shows a close-up of the mature inflorescence.
Figure 3:
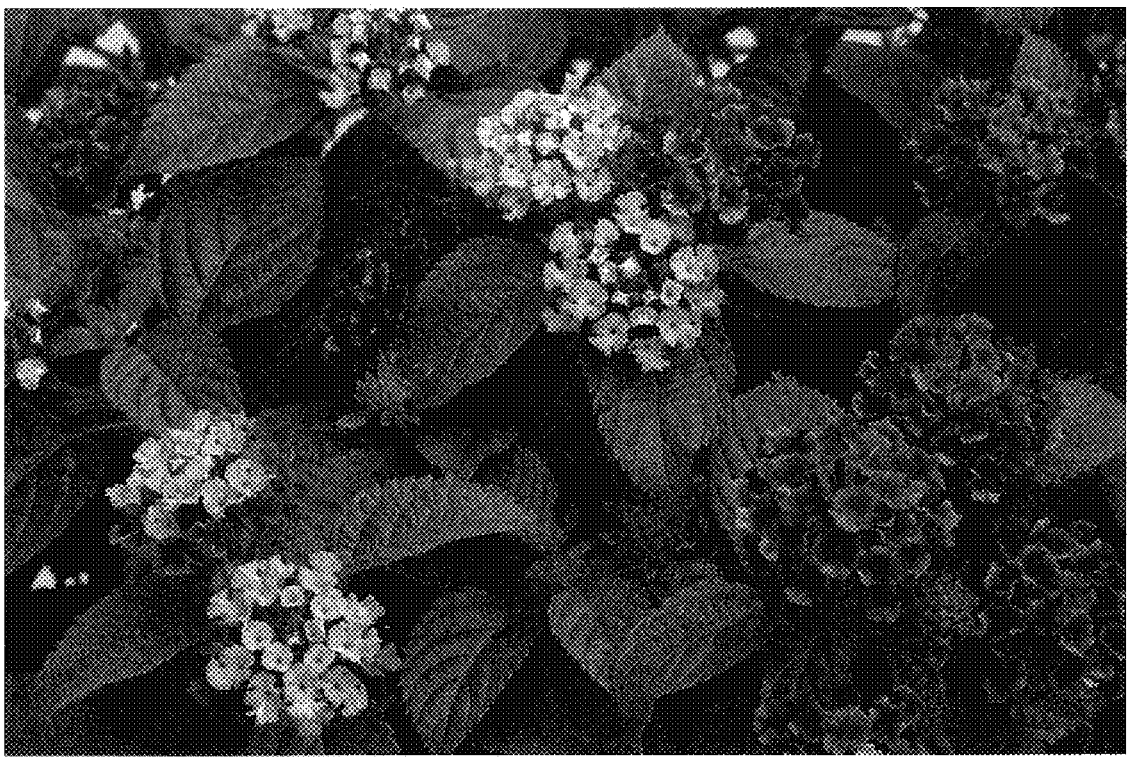
FIG. 3 shows a close-up of a portion of the whole plant.

The following detailed descriptions set forth the distinctive characteristics of 'Bante Rossa'. The data which define these characteristics were collected from asexual reproductions carried out in Hillscheid, Germany. The plant history was taken on 9- to 11-week-old plants, pinched once and grown 12-cm plastic pots in a greenhouse in Hillscheid, Germany in Summer 2005. Observations were made in early September 2005 when the plants were beginning to flower. Color readings were taken under natural light. Color references are primarily to The R.H.S. Colour Chart of The Royal Horticultural Society of London (R.H.S.) (2001 edition).

DETAILED BOTANICAL DESCRIPTION

Classification:
*Family.*—Verbenaceae.
*Botanical.*—*Lantana camara.*
*Common name* —. *Lantana.*

Parentage:
*Female parent.*—'22-1', a proprietary (unpatented) rose-flowered *lantana* plant.
*Male parent.*—'F13-1', a proprietary (unpatented) pink-flowered *lantana* plant.

Growth:

*Form.*—A shrub/perennial; the growing parts of the plant are herbaceous, while the plant base and the older stems are woody; commercially, it is grown as an annual.

*Growth and branching habit.*—Spreading and well-branched; pinching of the apices enhances the number of branches and results in a tighter plant habit.

*Height* (*measured from the top of the soil*).—24.1 cm.

*Width* (*horizontal plant diameter*).—17.5 cm.

*Time to produce a finished flowering plant.*—12- to 13-weeks for a 12-cm pot in the Spring.

*Outdoor plant performance.*—Use as bedding plants and in containers.

*Time to initiate and develop roots.*—24 days.

*Root description.*—Fibrous and self-branching.

Stems:

*Number of branches per plant.*—6.5.

*Length.*—18 cm to 22 cm.

*Diameter* (*measured from the midpoint*).—0.3 cm.

*Internode length.*—2.5 cm to 4.5 cm.

*Color.*—Immature (growing) stems: RHS 143C. Mature (woody) stems: RHS 165A (brown) with RHS 159A stripes.

*Anthocyanin.*—Absent.

*Texture.*—Covered with short pubescence.

Leaves:

*Arrangement.*—Opposite.

*Fragrance.*—The foliage has a lemon-like fragrance.

*Immature leaf.*—Color: Upper surface: RHS 143A. Lower surface: RHS 143C.

*Mature leaf.*—Color: Upper surface: RHS 137A (deep green). Lower surface: RHS 138A. Length: Up to 8.0 cm. Width: Up to 4.7 cm. Shape: Ovate. Apex: Acute. Base: Truncate to obtuse. Margin: Serrate. Texture: Somewhat rugose, slightly glossy and with fine pubescence. Venation: Pinnate. Venation color: RHS 145A for the lower surface; the upper surface is indistinct.

*Petioles.*—Length: 0.5 cm to 1.5 cm. Diameter: 0.2 cm. Color: RHS 143D (light-green). Texture: Pilose (relatively dense hair).

Flower buds:

*Shape.*—Tubular.

*Length.*—1.5 cm to 1.6 cm.

*Diameter* (*at the tip*).—0.5 cm to 0.6 cm.

*Color* (*at tight bud*).—Near RHS 20C (light yellow-orange) at the tip and RHS 47C (light-red) for the lower part.

Inflorescence:

*Blooming habit.*—Flowers continuously from Spring through Fall; flowers appear about 10 weeks after planting of rooted cuttings; inflorescences usually appear in pairs from a nodium with one inflorescence per leaf axil.

*Fragrance.*—None.

*Inflorescence type.*—Umbel-like; umbrella-shaped to semi-spherical and subtended by a ring of leaflets; the florets are sessile on an ovate receptacle.

*Horizontal diameter of inflorescence.*—5.0 cm to 5.5 cm.

*Vertical depth of inflorescence.*—2.0 cm to 2.5 cm.

*Number of inflorescences per plant.*—13.

*Number of florets per inflorescence.*—15 to 20.

*Peduncle.*—Length: Up to 8.5 cm. Diameter: 0.2 cm. Color: RHS 143B. Texture: Rough and covered with short pubescence. Pedicels.—None, flowers are sessile.

Flowers:

*Floret form.*—Composed of 5 mostly-fused petals which open outward and are salver-shaped and zygomorphic with a long tube-shaped base.

*Corolla diameter.*—1.2 cm to 1.5 cm.

*Floret depth.*—About 2.0 cm.

*Immature flower* (*face*).—Color: Upper surface: RHS 5A (yellow) or lighter. Lower surface: Mainly RHS 4D (cream).

*Mature flower* (*face*).—Color: General: Mostly purple-pink but variable from yellow to golden yellow (few). Upper surface: RHS 72C (purple-pink), RHS 9A (yellow) with RHS 8C at the margin or RHS 13A (golden yellow) with RHS 20C at the margin. Lower surface: RHS 75A to RHS 75B (pale purple) to RHS 76D (nearly white) for the purple-pink florets and RHS 8C or RHS 18C (light yellow-orange) for the yellow or golden yellow florets. Corolla tube: Length: 1.7 cm to 1.8 cm. Diameter (at opening): 0.2 cm to 0.25 cm. Color: Outer surface: RHS 47C or lighter for the yellow and golden yellow florets and RHS 55B to RHS N66D for the purple-pink florets. Inner surface: RHS 5A (yellow) or RHS 27D (pale cream-orange). Texture: With very short dense pubescence.

*Petals.*—Length of lobe: 0.3 cm to 0.5 cm. Diameter of lobe: 0.7 cm to 0.8 cm. Lobe shape: Salver-shaped. Apex: Rounded; largest petal is broadly acute. Base: Fused. Margin: Entire or shallowly crenate in parts. Degree of lobation: Moderate. Texture: Finely rugose.

*Calyx.*—General: Composed of 5 fused sepals forming a short tube around the base of the floret. Shape: Tube-shaped with two short lobes. Length: 0.3 cm. Diameter: 0.3 cm. Color: RHS 139D (pale green). Apex (of calyx lobe): Obtuse. Base (of sepals): Fused. Margin (of sepals): The tips are shallowly fringed. Texture: Densely pubescent.

Reproductive organs:

*Stamens.*—Quantity: 4, which protrude from the floret tube. Filament color: RHS 155A. Filament diameter: 0.1 cm. Filament length: About 1.0 cm. Anther color: RHS 1A (yellow). Anther length: 0.1 cm. Anther shape: Spindle-shaped. Pollen amount: Sparse. Pollen color: RHS 18A (yellow).

*Pistil.*—Quantity: One. Length: 0.6 cm. Style diameter: 0.1 cm. Stigma color: RHS N144A (greenish-yellow). Style color: RHS 155A (whitish) and RHS 185D (purple) in parts.

Fruit/seed set: A drupe resembling a blueberry; mature fruits are RHS 202A (black), glossy, nearly round, somewhat flattened and 0.7 cm in diameter.

Disease and insect resistance: None observed.

COMPARISON WITH PARENTAL AND COMMERCIAL CULTIVARS

'Bante Rossa' differs from the female parent '22-1' (unpatented) in that 'Bante Rossa' has mainly purple-pink, yellow, and golden yellow flowers, while '22-1' has rose flowers. Additionally, 'Bante Rossa' has larger inflorescences, an earlier flowering response, and a tighter plant habit than '22-1'.

'Bante Rossa' differs from the male parent 'F13-1' (unpatented) in that 'Bante Rossa' has mainly purple-pink, yellow, and golden yellow flowers, while 'F13-1' has pink flowers. Additionally, 'Bante Rossa' has larger inflorescences and a more compact and slightly shorter plant habit than 'F13-1'.

'Bante Rossa' differs from the commercial variety 'Robpatcow' (U.S. Plant Pat. No. 12,450) in that 'Bante Rossa' has mainly purple-pink, yellow, and golden yellow flowers, while 'Robpatcow' has mainly bright orange flowers. Additionally, 'Bante Rossa' has a more vigorous growth habit than 'Robpatcow'.

I claim:

1. A new and distinct cultivar of *lantana* plant as shown and described herein.

* * * * *